United States Patent

Wakabayashi et al.

[11] Patent Number: 5,294,280
[45] Date of Patent: Mar. 15, 1994

[54] GAS MEASURING DEVICE AND PROCESSING APPARATUS PROVIDED WITH THE GAS MEASURING DEVICE

[75] Inventors: Tsuyoshi Wakabayashi; Takenobu Matsuo; Shuji Moriya, all of Tokyo; Hidenobu Arimitsu, Kanagawa, all of Japan

[73] Assignees: Tokyo Electron Limited, Tokyo; Ebara Research Co., Ltd., Fujisawa, both of Japan

[21] Appl. No.: 904,556

[22] Filed: Jun. 26, 1992

[30] Foreign Application Priority Data

Jun. 28, 1991 [JP] Japan .................................. 3-183655
Jun. 28, 1991 [JP] Japan .................................. 3-183656
Jun. 28, 1991 [JP] Japan .................................. 3-183657

[51] Int. Cl.[5] ............................................ H01L 21/00
[52] U.S. Cl. .................................... 156/345; 156/626; 156/627; 118/712; 118/715; 118/724; 204/298.03; 204/298.32
[58] Field of Search .................. 156/345, 626, 627; 204/298.03, 298.32; 73/31.2, 31.7, 31.5; 427/8; 118/723, 715, 712, 724

[56] References Cited

U.S. PATENT DOCUMENTS

| | | | |
|---|---|---|---|
| 4,013,943 | 3/1977 | Chou et al. | 73/31.5 X |
| 4,267,023 | 5/1981 | Frant et al. | 73/31.2 X |
| 4,326,200 | 4/1982 | Bushman | 73/31.5 X |
| 4,994,158 | 2/1991 | Kiimalainen et al. | 73/23.2 X |
| 5,153,139 | 10/1992 | Volz-Thomas et al. | 73/31.7 X |

Primary Examiner—Thi Dang
Attorney, Agent, or Firm—Oblon, Spivak, McClelland, Maier & Neustadt

[57] ABSTRACT

A gas measuring device includes a dissolving unit for dissolving gas to be measured in solvent medium, a measuring unit for measuring the amount of ions generated when the gas to be measured is ionized in the liquid medium, and a calculating unit for calculating the amount of the gas to be measured from a value measured by the measuring unit.

10 Claims, 7 Drawing Sheets

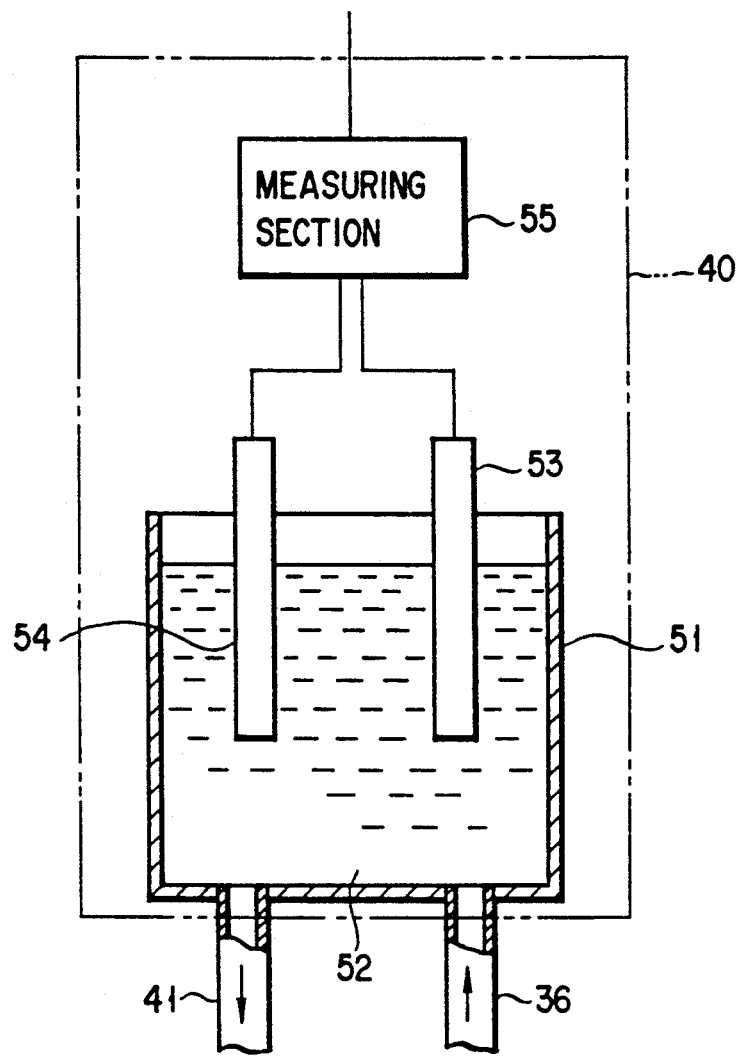
F I G. 3

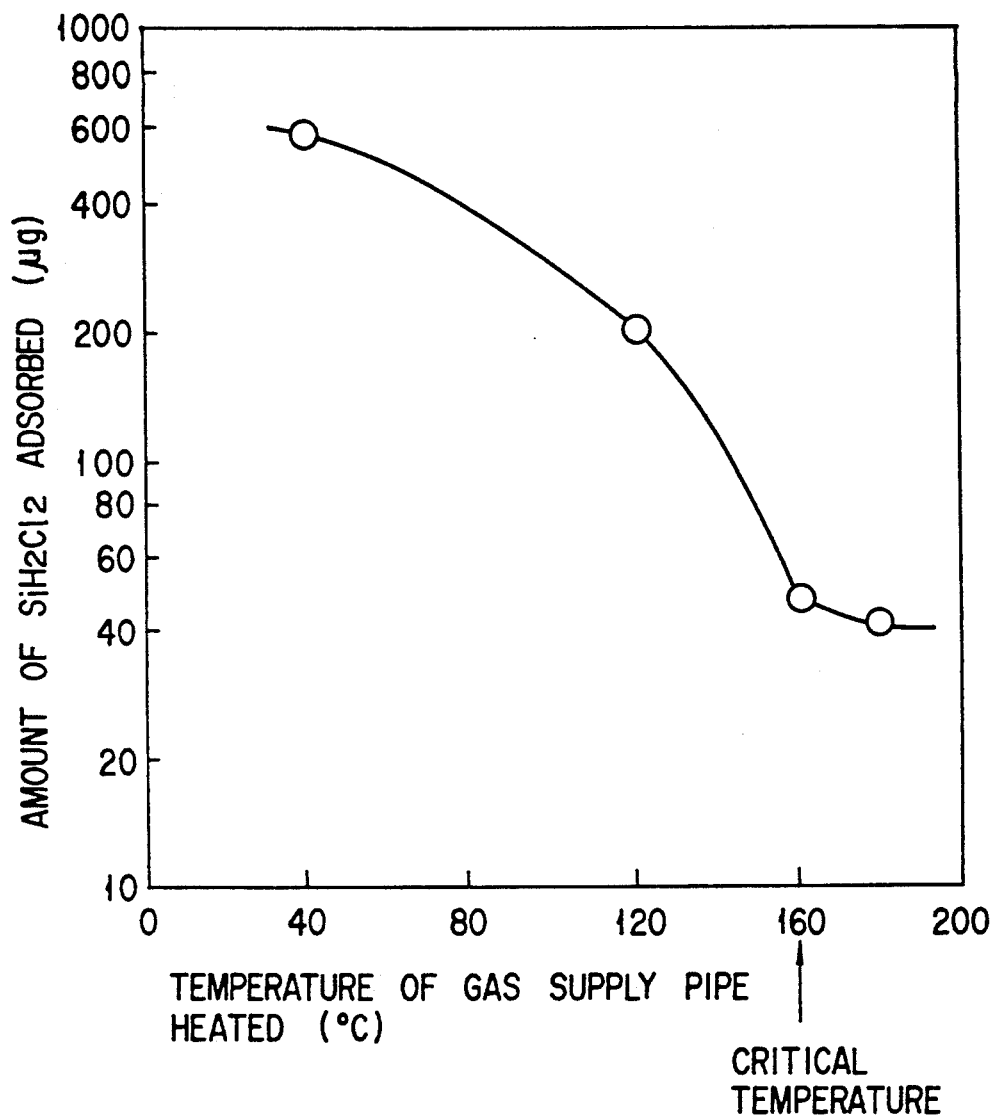
F I G. 4

| | EXHAUST (TOTAL 50 min) | TEMPERATURE OF GAS SUPPLY PIPE | AMOUNT OF REMAINING REACTIVE GAS |
|---|---|---|---|
| CASE 1 | V | 40 °C | 1400 μg |
| CASE 2 | V N2 V | 40 °C | 880 μg |
| CASE 3 | V N2 V | 160 °C | 280 μg |
| CASE 4 | V N2 V N2 V | 160 °C | 200 μg | ture of the gas supply pipe heated and the amount of $SiH_2Cl_2$ stuck to the gas supply pipe;
GAS MEASURING DEVICE AND PROCESSING APPARATUS PROVIDED WITH THE GAS MEASURING DEVICE

BACKGROUND OF THE INVENTION

1. Field of the Invention

The present invention relates to a gas measuring device suitable for use with the processing apparatus in which a certain process of process gas is applied to objects to be processed, and also relates to a processing apparatus provided with the gas measuring device.

2. Description of the Related Art

Most semiconductor manufacturing apparatuses including the heat treating apparatus, diffusing apparatus, etching apparatus, sputtering apparatus and others are intended to process the surface of objects to be processed such as semiconductor wafers by process gases supplied. They are exhausted after this surface process and their certain processes are then finished.

In the case of the heat treating apparatus of the batch type, for example, $SiH_2Cl_2$ gas is supplied as reaction gas into the reaction tube through the reactive gas supply pipe, Si film is formed on the surface of each of wafers positioned at the soaking zone in the reaction tube, and gas remaining in the reaction tube is then exhausted through the exhaust pipe by the vacuum pump connected to the exhaust pipe. The process is thus finished. After the finish of this process, purge gas such as inactive $N_2$ gas is introduced into the reaction tube through the reactive gas supply pipe to replace atmosphere in the reaction tube by $N_2$ gas. The semiconductor wafers which have been processed are then unloaded out of the reaction tube.

However, it has been found that the remaining reaction gas still discharged, though low in density, from the reaction gas supply pipe and adheres to the inner wall of the reaction tube and the surface of each of the processed objects, even when the reaction tube is purged by the purge gas such as $N_2$ gas. This remaining reaction gas creates harmful substances and particularly in the case of $SiH_2Cl_2$ gas it creates poisonous and corrodible HCl on the way of its reaction. It is therefore asked that HCl is measured even if its amount is extremely small. However, a device has not yet been provided to continuously measure such gas component that is low in density and extremely small in amount.

SUMMARY OF THE INVENTION

The present invention is therefore intended to meet the above-stated need.

Accordingly, an object of the present invention is to provide a gas measuring device capable of continuously measuring gas, low in density and extremely small in amount.

Another object of the present invention is to provide a processing apparatus provided with the gas measuring device on its gas supply or exhaust side.

According to an aspect of the present invention, there is provided a gas measuring device comprising dissolving means for dissolving gas to be measured in solvent medium; measuring means for measuring the amount of charged particles which are caused from the gas to be measured in the solvent medium; and calculating means for calculating the amount of the gas to be measured on the basis of a value measured by the measuring means.

According to another aspect of the present invention, there is provided a processing apparatus comprising a process vessel in which process gas is applied to an object or objects to be processed; a gas supply system through which the process gas is supplied into the process vessel; an exhaust system through which gas is exhausted from the process vessel; and a gas measuring device for measuring gas remaining in the apparatus; wherein said gas measuring device includes means for dissolving gas to be measured in solvent medium, means for measuring the amount of charged particles caused from the gas to be measured in the solvent medium, and calculating means for calculating the amount of the gas to be measured from a value measured by the measuring means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 shows a measuring instrument employed by the gas measuring device in FIG. 2;

FIG. 4 is a graph showing the relation between the temperature of the gas supply pipe heated and the amount of $SiH_2Cl_2$ stuck to the gas supply pipe;

DETAILED DESCRIPTION OF THE PREFERRED EMBODIMENTS

Figure 1:
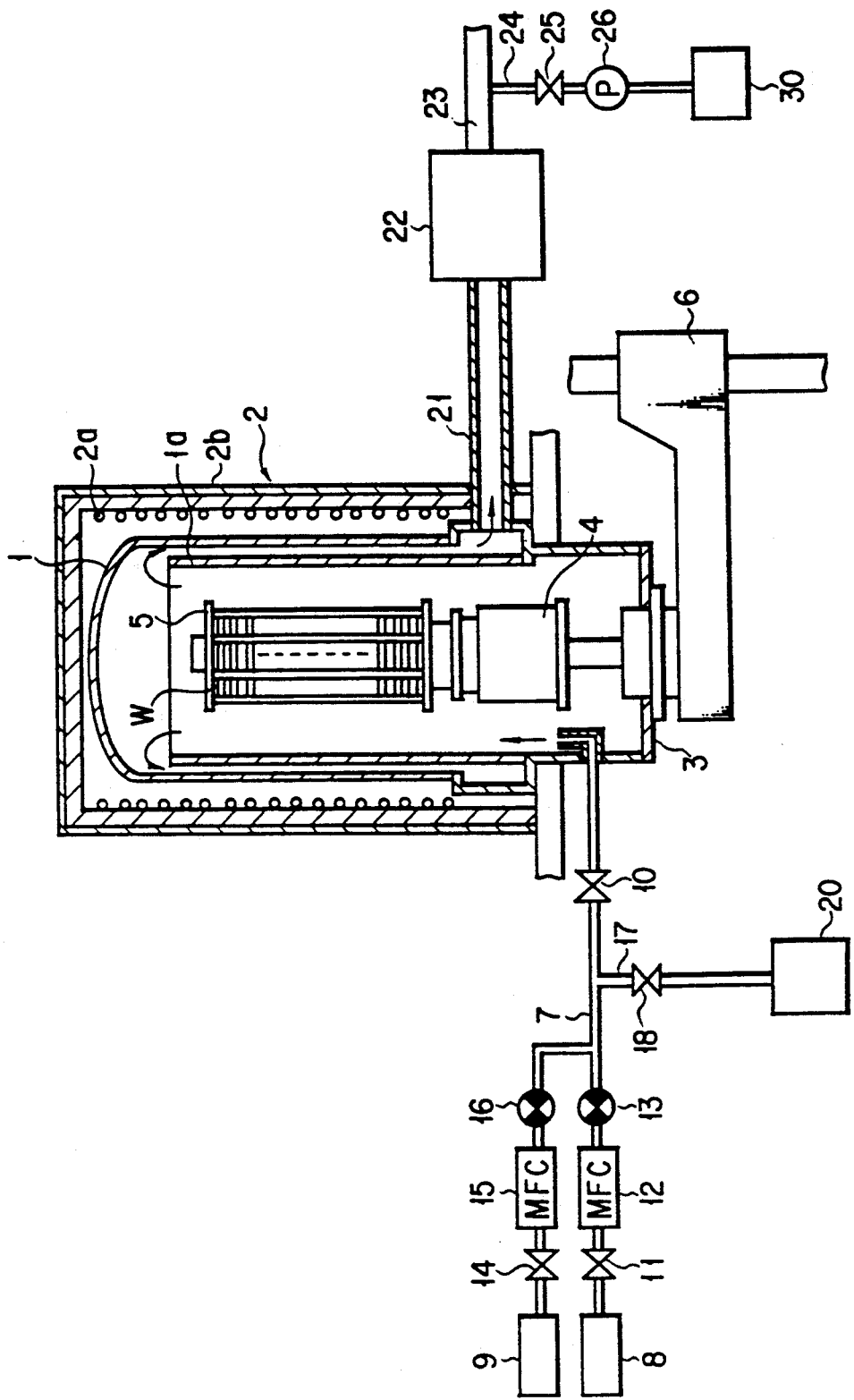
FIG. 1 is a sectional view showing a heat treating apparatus of the vertical type to which a gas measuring device according to the present invention has been applied.

A heat treating apparatus of the vertical type to which the gas measuring device according to an embodiment of the present invention has been applied will be described with reference to the accompanying drawings. FIG. 1 is a sectional view showing the heat treating apparatus. This heat treating apparatus includes a cylindrical reaction vessel 1 made of heat resistant material such as quartz and erected in its longitudinal direction, and a cylindrical heater 2 of the ohmic resistance heating type enclosing the reaction tube 1. The heater 2 includes an ohmic resistance wire 2a and a housing 2b. When current is applied to the ohmic resistance wire 2a, atmosphere in the reaction vessel 1 is heated to a certain temperature, so that a certain heat treatment can be applied to objects to be processed such as semiconductor wafers W in the reaction vessel 1.

An inner tube 1a is coaxially housed in the reaction vessel 1 and a cap-state support 3 is located at the bottom of the inner tube 1a. A heat insulating sleeve 4 is supported on the support 3. A wafer boat 5 in which a plurality of semiconductor wafers W to be processed are aligned is mounted on the heat insulating sleeve 4 in such a state that the wafers W are supported horizontally.

The support 3 can be moved up and down by an elevator 6 to load and unload the wafer boat 5 into and out of the reaction vessel 1. FIG. 1 shows the semiconductor wafers W loaded in the reaction tube 1. In this state, the support 3 serves as a cap, sealingly closing the reaction vessel 1. It is designed such that a soaking zone is formed at the portion where the wafers W are aligned in the inner tube 1a by the heater 2. When the wafer boat 5 is to be unloaded out of the reaction vessel 1, the cap-state support 3 is moved down by the elevator 6.

One end of a gas supply pipe 7 is connected to the lower side wall of the reaction vessel 1 and the other end thereof to reaction gas source 8 and purge gas supply source 9. The gas supply system is accommodated in a casing (not shown) and separated from reaction vessel 1 by about 3m. Accordingly, the length of the pipe 7 is also about 3m.

Reaction gas such as $SiH_2Cl_2$ is introduced from the reactive gas supply source 8 into the reaction. vessel 1 through the gas supply pipe 7. The predetermined process is then applied to the wafers W in the reaction vessel 1, whose atmosphere has been heated to the certain temperature, to form CVD film on each of the wafers W.

On the other hand, purge gas such as $N_2$ gas or $H_2$ gas is introduced from the purge gas supply source 9 into the reaction vessel 1 through the gas supply pipe 7.

A valve 10 is attached to the gas supply pipe 7 on the side of the reaction tube 1. The gas supply pipe 7 is branched on its way to the reactive gas supply source 8 and the purge gas supply source 9. A valve 11, a mass flow controller 12 and an electromagnetic valve 13 are attached to the pipe branched to the reactive gas supply source 8. A valve 14, a mass flow controller 15 and an electromagnetic valve 16 are attached to the pipe branched to the purge gas supply source 9.

A pipe 17 is connected to the gas supply pipe 7 and a gas measuring device 20 which will be later described in detail, is connected to the pipe 17 via a valve 18.

An exhaust pipe 21 is connected to the lower side wall of the reaction tube 1 and an exhaust pump 22 is connected to the exhaust pipe 21. The flow of reaction gas can be created in the reaction tube 1 while exhausting the reaction tube 1 by the exhaust pump 22.

A gas exhaust pipe 23 is connected to the exhaust pump 22 and a gas measuring device 30 which is identical in structure to the device 20 is connected to the pipe 23 through a valve 25 and a gas supply pump 26.

Figure 2:
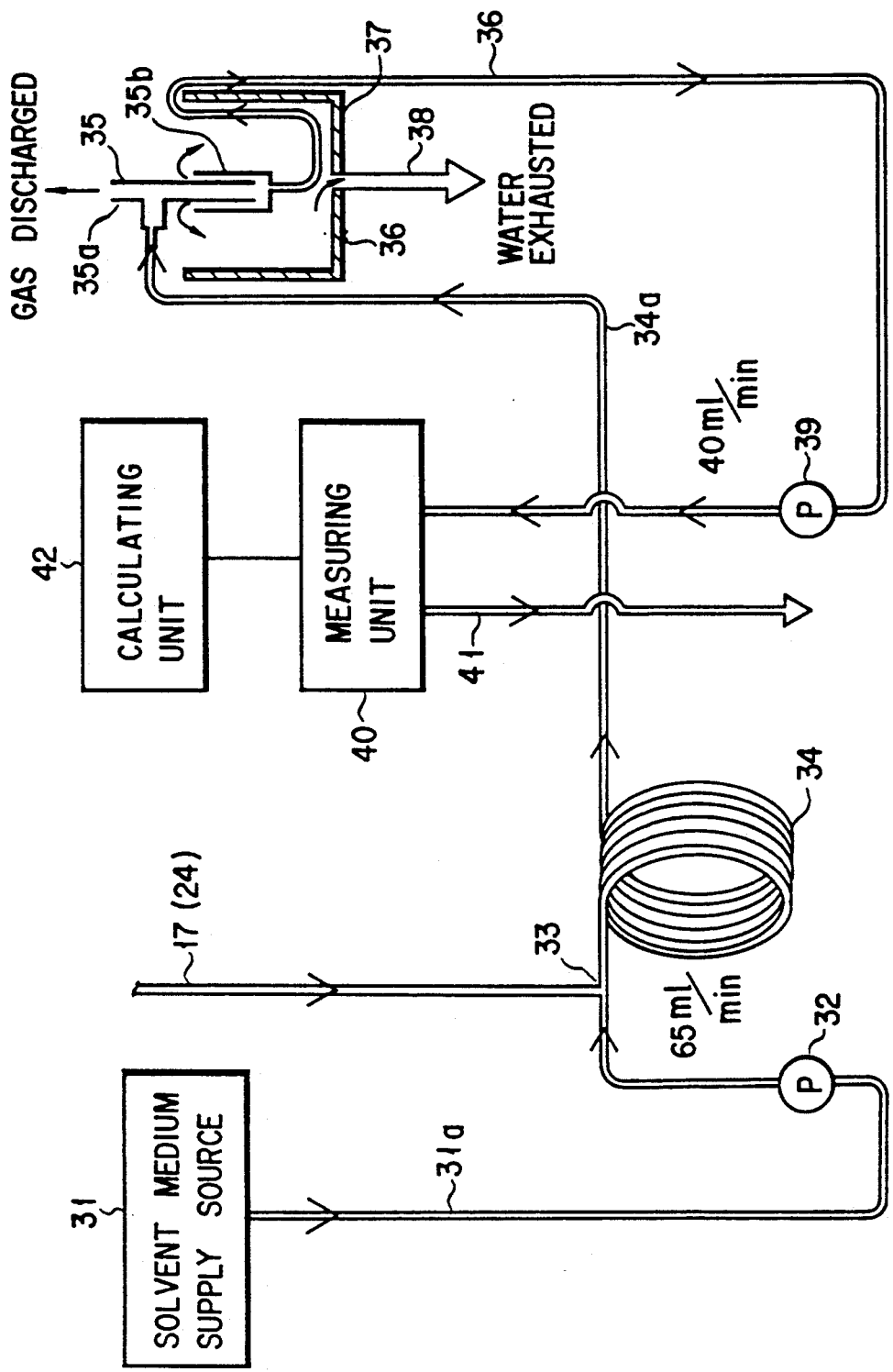
FIG. 2 shows an arrangement of the gas measuring device according to an embodiment of the present invention.

Referring to FIG. 2, it will be described how each of the gas measuring devices 20 and 30 is designed. Each gas measuring device 20 or 30 has a solvent medium supply source 31 from which solvent medium such as pure water is supplied. A pipe 31a is connected to the solvent medium supply source 31. A pressure pump 32 is attached to the pipe 31a so as to pressure-feed the solvent medium through the pipe 31a. The solvent medium which has been pressure-fed through the pipe 31a is mixed at a mixing point 33 with gas which includes quite a small amount of gas to be measured (such as $SiH_2Cl_2$) and purge gas such as $N_2$ purge gas supplied through the pipe 17 or 24, thereby forming a mixture. A matter in which only the gas to be measured can be dissolved is used as the liquid medium (pure water when the gas to be measured is $SiH_2Cl_2$ and the purge gas is $N_2$).

Only the gas to be measured in the mixture is completely dissolved in the solvent medium while the mixture is flowing through a spirally-wound pipe 34.

The mixture is pressure-fed into a separator 35, passing through a linear pipe 34a continuous from the pipe 34.

The gas of the mixture other than the gas to be measured, for example, $N_2$ purge gas is discharged into the air through an open top 35a of the separator 35. The remaining gas is supplied from an outer vessel 35b into a measuring unit 40 by a pump 39, passing through a pipe 36. The solvent medium fed from the separator 35 is received in the outer vessel 35b and the solvent medium of such an amount that corresponds to the difference between the amount of the solvent medium supplied to the outer vessel 35b and its amount passed through the pipe 36 is over-flowed into a container 37 arranged outside the outer vessel 35b and then exhausted through a pipe 38. This prevents the solvent medium from taking air into it while being supplied to the measuring unit 40. When the amount of the solvent medium pressure-fed by the pump 39 is set smaller than that supplied to the separator 35 in this manner, the liquid medium can be stably supplied to the measuring unit 40 even if the amount of the liquid medium pressure-fed by the pump 39 is reduced because of change in current applied from a power source to the pump 39.

Amount of ions as charged particles of the to-be-measured gas dissolved in the liquid medium are measured by the measuring unit 40. When the to-be-measured gas is, for example, $SiH_2Cl_2$, ions to be measured are chloride ions ($Cl^-$). The chloride measuring instrument (made by Orio Co.), for example, is used as the measuring unit 40 in this case. The amount of chloride ions ($C^-$) to be measured is measured by, for example, the chloride measuring instrument as the measuring unit 40 and these amounts thus measured are outputted as electric signals. In the case of the chloride measuring instrument shown in FIG. 3, the solvent medium is stored in a container 51 through the pipe 36 and a $C^-$ selective electrode 53 and a reference electrode 54 are immersed in the solvent medium in the container 51. Therefore, those changes in current flowing between these two electrodes 53 and 54 which are caused by $Cl^-$ are outputted as electric signals through a measuring section 55.

The solvent medium is continuously supplied to the measuring unit 40 through the pipe 36 and also continuously exhausted through a pipe 41.

Electric signals are applied from the measuring unit 40 to an calculating unit 42 in which a value for converting the measuring value is previously stored. A certain arithmetical calculation relating to the valve for converting and an electric signal inputted is thus conducted in the calculating unit 42 to calculate an absolute magnitude of the gas to be measured dissolved in the liquid medium.

Processing steps conducted in the heat treating apparatus shown in FIG. 1 will be described in a case where the reactive gas is $SiH_2Cl_2$, the purge gas is $N_2$ and the solvent medium is pure water.

The elevator 6 is lowered and the wafer boat 5 in which the semiconductor wafers W to be processed are housed is mounted on the heat insulating sleeve 4 on the support 3. The elevator 6 is lifted to load the wafer boat 5 into the reaction vessel 1. The reaction vessel is sealingly closed by the cap-state support 3.

Current is then applied to the ohmic resistance wire 2a of the heater 2 to heat atmosphere in the reaction vessel 1 in such a way that the portion where the wafers W are aligned are uniformly heated to a temperature of, for example, 800° C. in the reaction tube 1 so as to form CVD film on each of the semiconductor wafers W. The reaction tube 1 is then exhausted to a certain vacuum for example, $1 \times 10^{-3}$ Torr.

The valve 10 is made open and the reaction gas $SiH_2Cl_2$ of 200 SCCM is introduced from the reactive gas supply source 8 into the reaction vessel 1 through the gas supply pipe 7. The pressure of the reaction gas is kept at 1 Torr. The gas flow of the reaction gas is uniformly created on the surface of each of the semiconductor wafers W in the reaction vessel 1 to form Si film on them.

Gas resulting from the reaction is exhausted as waste gas through the exhaust pipe 21 by the exhaust pump 22.

This process is conducted for a certain time period, for example, 60 minutes, and the valve 10 is then closed to stop the supply of the reaction gas. The film forming process is thus stopped.

The valve 11 is closed and the valve 14 and 10 are opened to introduce the purge gas $N_2$ from the purge gas supply source 9 into the reaction vessel 1 through the gas supply pipe 7. The reaction tube 1 is exhausted while filling the reaction tube 1 and the gas supply pipe 7 with the $N_2$ gas. The atmosphere in the reaction tube 1 is thus replaced by the $N_2$ gas of atmospheric pressure and the purging of the reaction tube 1 is finished. The semiconductor wafers W which have been processed are then unloaded out of the reaction vessel 1.

Typically, however, even after the purging process, reaction gas component stuck to inner walls of the reaction vessel 1 and the gas supply pipe 7 is discharged, though quite small an amount, as harmful remaining gas. Particularly on unloading the semiconductor wafers W out of the reaction vessel 1, this measuring gas is discharged into the clean room, thereby causing workers to be forced to work in the atmosphere of harmful gas. In addition, undesirable effects are added to the semiconductor wafers, causing dust to be created and the formed film on the wafers W to be deteriorated.

In order to prevent this, the above-mentioned gas measuring devices 20 and 30 are provided. When these gas measuring devices are provided, the remaining gas can be continuously measured, and next process can be carried out after it is confirmed that the discharged amount of remaining gas is reduced.

In the case of the gas measuring device 20, pure water supplied from the solvent medium supply source 31 at a flow rate of 65 ml/min, for example, and $N_2$ purge gas supplied through the pipe 17 at 100 SCCM, for example, are mixed at the mixing point 33 and $SiH_2Cl_2$ gas to be measured is dissolved in the pure water while this mixture is flowing through the sprially-wound pipe 34 which has an inner diameter of 5 mm, for example, and a length of 5 m, for example. The $N_2$ gas is then separated from the mixture by the separator 35 and the mixture from which the $N_2$ gas has been thus separated is pressure-fed into the measuring unit 40 at a flow rate of 40 ml/min by the pump 39. $Cl^{31}$ of $SiH_2Cl_2$ gas is measured by the measuring unit 40 and the amount of $SiH_2Cl_2$ gas is calculated on the basis of the value thus obtained by the calculating unit 42.

The reason why this gas measurement becomes possible resides in that the following chemical reaction is caused when $SiH_2Cl_2$ is dissolved in pure water.

$$SiH_2Cl_2 + H_2O \rightarrow SiO + 4H^+ + 2Cl^-$$

In other words, the amount of the to-be-measured $SiH_2Cl_2$ gas supplied through the pipe 17 is proportional to the amount of $C^-$ caused when $SiH_2Cl_2$ is ionized in the pure water. When the amount of $C^-$ is measured by the measuring unit 40, therefore, the amount of the to-be-measured $SiH_2Cl_2$ can be measured.

The $SiH_2Cl_2$ is liquid and adsorptive at low temperature such as room temperature. Therefore, the liquid $SiH_2Cl_2$ sticks to the gas supply pipe 7, and when heated to high temperature, it is thermally cracked to particulates and gas, though quite a little, and the amount of these particulates and gas can be measured by the above-described gas measuring device 20.

When the amount of the certain gas is continuously measured in this manner by the gas measuring device, times at which the attached portions of the gas measuring (for example, gas supply pipe 7 and gas exhaust pipe 23) apparatus must be cleaned can be quickly found, and when these pipes 7 and 23 are cleaned by plasma and etching gas at the times found, the film forming process can be stably conducted. Further, the above-described gas measuring device can measure gas in terms of ppm and ppb, thereby making it possible to previously prevent any dust, even though extremely small in amount, from being caused. This enables the productivity of super LSIs to be remarkably enhanced in their manufacturing process.

When gas to be measured is difficultly dissolved in solvent medium, it is preferable that a matter which accelerates dissolving of the gas to be measured and generating charged particles in the solvent medium is previously added to the solvent medium and that the matter is contacted with the gas to be measured. In a case where gas to be measured is NOx (NO or $NO_2$), an oxidizing agent such as hydrogen peroxide ($H_2O_2$) is added, as this matter, to solvent medium (for example pure water). As the result, NOx is ionized to $NO_2^-$ and $NO_3^-$, which can be easily detected by the gas measuring device. This matter can be decomposed and removed by adding a reducing agent, for example. Even when this matter is added to the liquid medium, therefore, it does not act to make measurement accuracy low.

When gas to be measured is extremely small in amount, solvent medium including the gas is thickened by thickening means such as ion exchange. The liquid medium thus thickened is supplied to a separator which uses chromatography. Those charged particles which are to be measured, said charged particles being successively detected through the separator, are measured.

Another embodiment of the present invention will be described.

According to this embodiment, it is intended to avoid any disadvantages caused when the heat treatment is carried out using process gas such as $SiH_2Cl_2$ which is liquid at environmental temperature (usually ranging from 10° C. to 30° C.). When it is used, this liquid adheres to inner walls of the gas supply and exhaust pipes, thereby causing particles and the gas to be undesirably leaked. In addition, it causes various troubles to force the heat process system to be stopped. It is therefore needed to prevent the gas from adhering to inner walls of the pipes.

According to the second embodiment, therefore, means for heating the reaction gas are attached to the heat treating apparatus to heat reaction gas to a temperature higher than the critical temperature of the gas in order to prevent the gas component adhesion when such gas that is liquid at environmental temperature is used as reaction gas.

The reason why such means are added resides in the finding that the adsorbing amount of reaction gas component becomes extremely small when the reaction gas is heated to a temperature higher than its critical temperature. This will be described with reference to FIG. 4. FIG. 4 is a graph showing the relation between temperatures to which the gas supply pipe is heated and the amount of $SiH_2Cl_2$ adsorbed. The amount of $SiH_2Cl_2$ adsorbed can be obtained as follows: Heaters are arranged round the gas supply pipe to heat the pipe to a certain temperature. The predetermined heat process is conducted and purge gas is then introduced into the reaction vessel through the gas supply pipe and exhausted out of the reaction vessel through the gas exhaust pipe. The amount of $SiH_2Cl_2$ in the purge gas exhaust is calculated and the amount thus obtained is regarded as the amount of $SiH_2Cl_2$ adsorbed.

As apparent from FIG. 4, the amount of $SiH_2Cl_2$ adsorbed is 600 μg when the gas supply pipe is heated to 40° C. When it is heated to 160° C. which is the critical temperature of the gas, however, the amount of $SiH_2Cl_2$ adsorbed is reduced to 50 μg, lower than a tenth. Even when it is heated to a temperature higher than 160° C., significant change cannot be found in the amount of $SiH_2Cl_2$ adsorbed. When $SiH_2Cl_2$, which serves as the reaction gas, is heated to a temperature higher than its critical temperature, therefore, its amount adsorbed can be made extremely small. The same thing can be said about other gases which are liquid at environmental temperature and which serve as the reaction gas.

Figure 5:
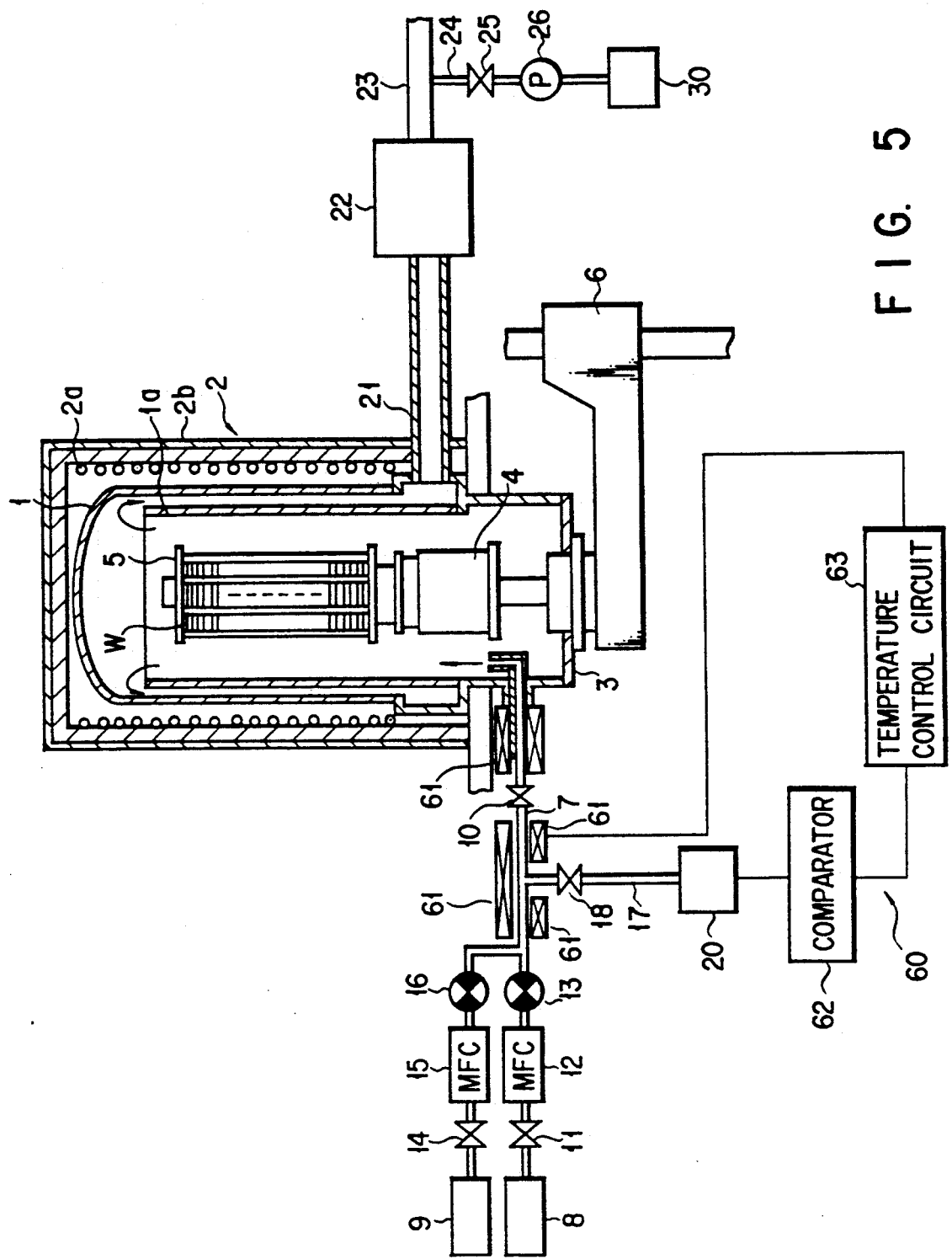
FIG. 5 is a sectional view showing another heat treating apparatus to which the gas measuring device according to the present invention has been applied.

FIG. 5 is a sectional view showing the heat treating apparatus according to the second embodiment of the present invention. This heat treating apparatus is fundamentally the same in structure as the one shown in FIG. 1. Therefore, the same components as those in the heat treating apparatus shown in FIG. 1 will be denoted by same reference numerals and description of these components will be omitted.

The heat treating apparatus includes heaters 61 arranged around the gas supply pipe 7 to heat the pipe, and a control section 60 for controlling, responsive to signals applied from the gas measuring device 20, the temperature of the pipe 7 within a certain range of temperatures higher than the critical temperature of the reaction gas. The control section 60 is provided with a comparator 62 and a temperature control circuit 63. The comparator 62 is connected to the gas measuring device 20 and it includes set values representing amounts of reaction gas adsorbed corresponding to the amount when the pipe 7 is heated higher than the critical temperature of reaction gas based on the results shown in FIG. 4. It compares an amount of reaction gas in the purge gas measured by the gas measuring device 20 with the set values and applies the result thus obtained to the temperature control circuit 63. When the measured value is in a range of the set values, the temperature of the pipe is kept as it is, but when out of the range of the set values, control signal is applied from the temperature control circuit 63 to the heaters 61 to keep the measured value in the range of the set values. The temperature of gas supply pipe 7 can be thus kept higher than the critical temperature of reaction gas, thereby preventing reaction gas component from sticking to the inner wall of the gas supply pipe 7. The generating of particles and various other troubles which will be caused at the gas supply line can be thus more reliably prevented.

In order to heat reactive gas higher than its critical temperature, it may be arranged that the temperature of the heaters 61 is detected independently of the gas measuring device and controlled directly.

Figures 6, 7:
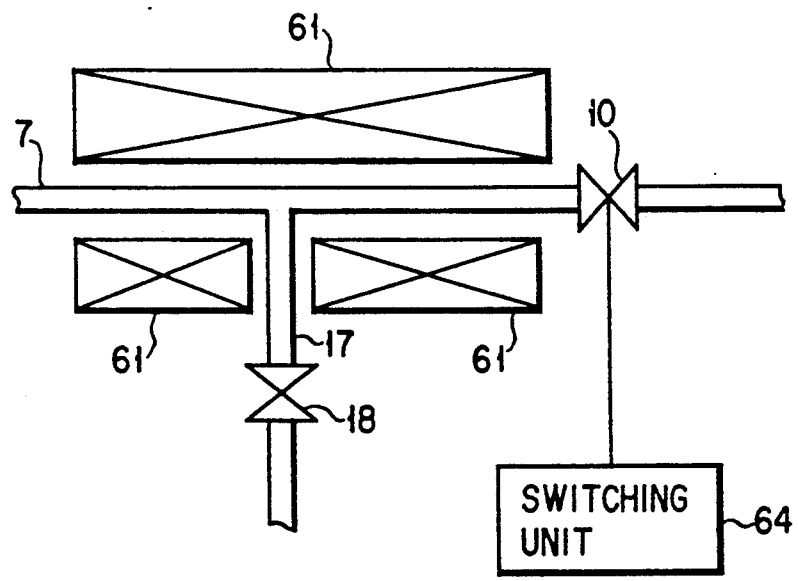
FIG. 6 is a sectional view showing a further heat treating apparatus to which the gas measuring device according to the present invention has been applied.
FIG. 7 shows the relation between manners of exhausting the reaction vessel and the amount of remaining reaction gas in the apparatus of FIG. 6.

It takes a long time to completely exhaust reactive gas which has been adsorbed on the inner wall of the pipe line such as the gas supply pipe. As the result, the throughput of the system is lowered. It is therefore needed that the gas component remaining in the pipe line is quickly exhausted. FIG. 6 shows an arrangement to meet this need. As shown in FIG. 6, switching unit 64 for automatically opening and closing the valve 10 is added to the system shown in FIG. 5.

When the gas supply pipe 7 is heated higher than the critical temperature of reactive gas, the amount of reaction gas adsorbed can be made small, as described above. In order to quickly exhaust the gas component remaining in the pipe line, it is preferable that the gas supply pipe 7 is heated higher than the critical temperature of reaction gas as shown in FIG. 5. In order to more quickly exhaust it, the valve 10 is opened and closed at a certain interval by the switching unit 64 to intermittently supply purge gas into the reaction tube 1, while exhausting the reaction vessel 1 by the exhaust pump.

FIG. 7 shows the manner of exhausting the reaction vessel, the temperature of the gas supply pipe and the amount of reaction gas left in the reaction vessel after the finish of process. Symbol V in FIG. 7 represents that the reaction vessel is only exhausted by the exhaust pipe and symbol $N_2$ denotes that purge gas is introduced into the reaction vessel while exhausting it. In case 1 shown in FIG. 7, the temperature of the gas supply pipe 7 was kept 40° C. and the reaction vessel was only exhausted for fifty minutes without introducing any purge gas into it. The amount of the remaining gas measured by the gas measuring device 20 was 1400 μg. In a case 2, the temperature of the gas supply pipe 7 was also kept 40° C. same as in the case 1. The reaction vessel was only exhausted at first, the valve 10 was then opened by the switching unit 64 to introduce purge gas $N_2$ into the reaction tube and it was again closed by the switching unit 64 to allow the reaction tube to be only exhausted. The amount of the remaining gas was reduced to 880 μg in this case 2. In case 3 where the same conditions as in the case 2 were kept except that the temperature of the gas supply pipe 7 was raised to 160° C., the amount of the remaining gas was more remarkably reduced to 280 μg. In a case 4 where the valve 10 is opened and closed at an interval of 10 minutes by the switching unit 64 while keeping the gas supply pipe 7 at the temperature of 160° C., the amount of the remaining gas was still more remarkably reduced to 200 μg. It has been confirmed from the above that the remaining gas component can be quickly exhausted when that portion of the system in which the reaction gas remains is heated to a temperature higher than the critical temperature of the reaction gas and the purge gas is intermittently introduced into the reaction vessel while exhausting the tube.

It is preferable that the switching unit 64 automatically applies opening and closing signals to the valve 10 responsive to a program previously set. Further, the remaining gas can be similarly and quickly exhausted even when other portions of the system such as the gas exhaust pipe, in which the reaction gas remains, are heated as well.

Figure 8:
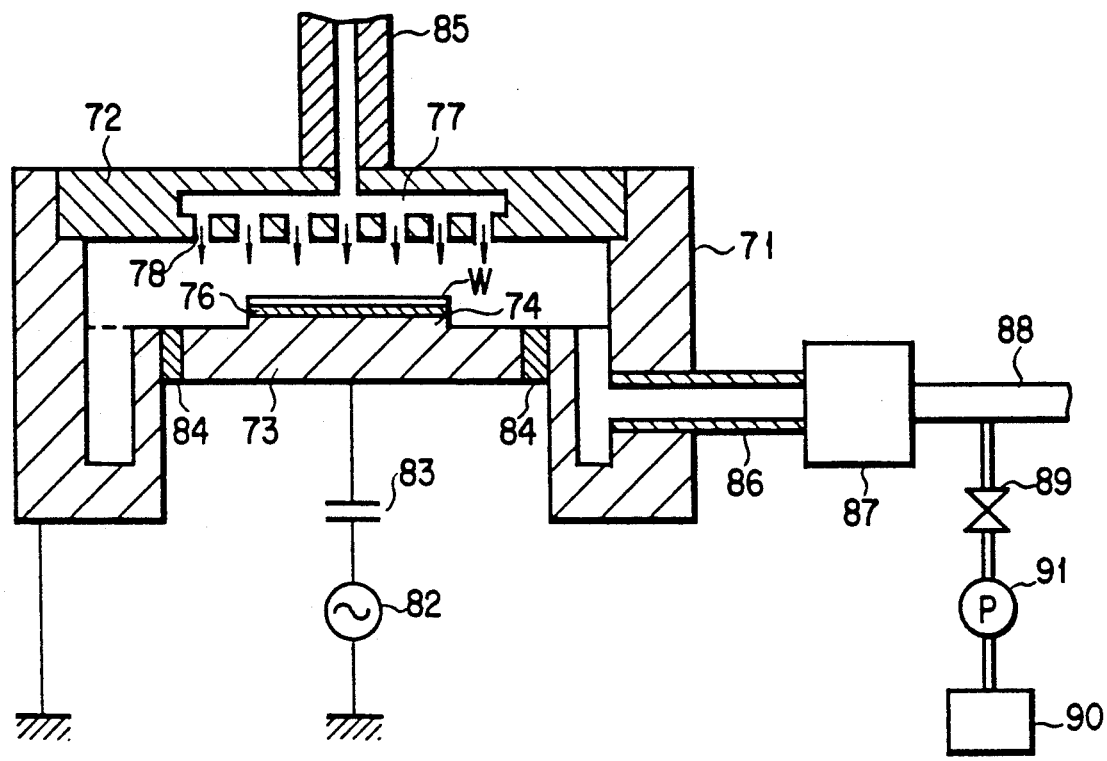
FIG. 8 is a sectional view showing a plasma etching apparatus to which the gas measuring device according to the present invention has been applied.

An example wherein the gas measuring device of the present invention is attached to the plasma etching apparatus will be described. FIG. 8 is a sectional view showing the plasma etching apparatus provided with the gas measuring device. The etching system includes a process vessel 71, paired electrodes 72 and 73 and a power supply 82.

The process vessel 71 is intended to etching-process the semiconductor wafer W therein. It can be kept at a vacuum when it is exhausted through an exhaust pipe 86, which is connected to its lower side wall, by an exhaust pump 87. It is provided with a pair of the electrodes opposed to each other. As shown in FIG. 8, for example, its top serves as the upper electrode 72 and its bottom as the lower electrode 73. Its side wall is insulated from the electrode 73 by an insulating member 84. The electrode 73 has a disk-like projection (or susceptor) 74 on the top center thereof and the semiconductor wafer W is supported on this projection 74. In order to reliably support the semiconductor wafer W on the projection 74, a chuck mechanism such as electrostatic chuck 76 is provided on the projection 74 to suck the semiconductor wafer W onto it.

A disk-like space is formed in the upper electrode 72, opposing to the projection 74, and a plurality of gas distributing holes 78 are formed in the bottom of the space 77, communicating with the space 77 and with the inside of the process vessel 71. A gas supply pipe 85 is connected to the space 77 and etching gas supplied through the gas supply pipe 85 is introduced into the process vessel 71, passing through the space 77 and the gas distributing holes 78. Means for heating process gas higher than normal temperature may be provided if necessary and the process gas may be supplied into the process vessel 71 through the heating means.

The lower electrode 73 includes a temperature adjuster (not shown) to set the, semiconductor wafer W at a desired temperature (or within a temperature range of 150° C. to 300° C., for example).

The RF power supply 82 is connected to the lower electrode 73 via a capacitor 83 and it is earthed. High frequency power of 13.56 MHz, for example, is supplied from the power supply 82 between the upper 72 and the lower electrode 73. The upper electrode 72 is earthed and high frequency power is supplied to the lower electrode 73 in this case, but it may be arranged that the lower electrode 73 is earthed and that high frequency power is supplied to the upper electrode 72.

The gas exhaust pipe 88 is connected to the exhaust pump 87 and gas measuring device 90, identical in structure to each of the above-described gas measuring devices 20 and 30. Gas measuring device 90 is connected to the pipe 88 via a valve 89 and a gas supply pump 91.

When the etching process is performed on the semiconductor wafer W in the above-described apparatus the wafer W is carried into the process vessel 71 and sucked onto the electrostatic chuck 76. The process vessel 71 is exhausted through the exhaust pipe 86 by the exhaust pump 87 and inside of the vessel 51 is set, for example, at 10 Torr.

The process gas is supplied from the space 77 into the process vessel 71, passing through the gas distributing holes 78, and high frequency power is supplied from the power supply 82 between the upper 72 and the lower electrode 73. The etching gas is thus made plasma to etch the semiconductor wafer W.

After the finish of this etching process, the etching gas supply is stopped and the process vessel 71 is exhausted by the exhaust pump while introducing the purge gas into the process vessel through the gas supply pipe 85. The amount of the etching gas remaining in the exhausted gas can be continuously measured by the gas measuring device 90 for this while. Therefore, the finish time of purging and the time to make maintenance relative to the apparatus can be found, thereby enabling the etching process to be quickly and stably conducted.

Although the solvent medium which is used by the gas measuring device is pure water in the above-described embodiments, other solvent mediums for example, alcohol may be used.

Further, gas to be measured is not limited to the above-mentioned one but particularly corrodible gases can be effectively measured. In a case where HBr is present as the remaining gas in the exhaust gas, for example, it is dissolved in pure water to allow bromic acid ions to be measured. The gas measuring device of the present invention can measure these corrodible gases in real time.

Still further, the gas measuring device has been attached to each of the gas supply and exhaust pipes in the above-described embodiments, but it may be attached to the process vessel to measure gas remaining therein.

Still further, the gas measuring device of the present invention has been applied to the heat treating apparatus and etching apparatus, but it may be applied to any of the processing apparatus such as the plasma CVD system in which gas is used. In addition, the uses of the gas measuring device is not limited to the above processing apparatus, and it can be widely used in the field where extremely small amounts of gas must be detected.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A processing apparatus comprising:
   a process vessel in which process gas is applied to an object or objects to be processed;
   a gas supply system through which the process gas is supplied into the process vessel;
   an exhaust system through which gas is exhausted from the process vessel; and
   a gas measuring device for measuring gas remaining in the apparatus;
   wherein said gas measuring device includes means for dissolving gas to be measured in a solvent medium, means for measuring the amount of charged particles generated from the gas to be measured in the solvent medium, and calculating means for calculating the amount of the gas to be measured from the amount of charged particles measured by the measuring means.

2. The processing apparatus according to claim 1, wherein said gas measuring device is attached to the gas supply system.

3. The processing apparatus according to claim 2, further comprising heating means for heating the process gas, which is liquid at environmental temperature, to a temperature higher than the critical temperature of said process gas.

4. The processing apparatus according to claim 3, wherein said gas supply system includes supplying means for supplying purge gas into the process vessel after the process by the process gas is finished and switching means for starting and stopping the supply of the purge gas to intermittently supply said purge gas into the process vessel while exhausting the process vessel through the exhaust system.

5. The processing apparatus according to claim 2, wherein said gas measuring device is attached to the exhaust system.

6. The processing apparatus according to claim 1, wherein said processing apparatus is a heat treating apparatus in which CVD film is formed on an object or objects to be processed.

7. The processing apparatus according to claim 6, wherein said gas measuring device is attached to the exhaust system.

8. The processing apparatus according to claim 7, wherein said processing apparatus is an etching apparatus in which an object to be processed is etched by etching gas.

9. A processing apparatus according to claim 1 wherein said gas measuring device further includes means for separating gas components except the gas to be measured from the solvent medium.

10. The processing apparatus according to claim 1 wherein said gas measuring device further includes electrodes for selectively detecting ions generated from the gas to be measured in the solvent medium.

* * * * *